United States Patent
Rhodes (10) Patent No.: US 7,318,887 B2
(45) Date of Patent: Jan. 15, 2008

(54) SOLID STATE REFERENCE ELECTRODE

(75) Inventor: Michael L. Rhodes, Richfield, MN (US)

(73) Assignee: Honeywell International Inc., Morristown, NJ (US)

( * ) Notice: Subject to any disclaimer, the term of this patent is extended or adjusted under 35 U.S.C. 154(b) by 824 days.

(21) Appl. No.: 10/681,440

(22) Filed: Oct. 8, 2003

(65) Prior Publication Data

US 2005/0077179 A1    Apr. 14, 2005

(51) Int. Cl.
*G01N 27/30* (2006.01)
(52) U.S. Cl. .................. 204/435; 204/400; 257/253
(58) Field of Classification Search ............... 204/400, 204/435; 257/253
See application file for complete search history.

(56) References Cited

U.S. PATENT DOCUMENTS

| | | | |
|---|---|---|---|
| 3,926,764 A | 12/1975 | Ruzika et al. | |
| 4,269,682 A | 5/1981 | Yano et al. | |
| 4,708,905 A * | 11/1987 | Yoshii et al. | 428/216 |
| 5,160,597 A * | 11/1992 | Colapicchioni et al. | 204/403.06 |
| 5,271,820 A | 12/1993 | Kinlen et al. | |
| 6,094,335 A * | 7/2000 | Early | 361/303 |
| 6,426,861 B1 * | 7/2002 | Munshi | 361/312 |
| 6,483,694 B1 * | 11/2002 | Monden et al. | 361/523 |

2002/0065332 A1   5/2002   Choi et al.

FOREIGN PATENT DOCUMENTS

EP          0155068       9/1985
WO     WO 96/35116     11/1996

OTHER PUBLICATIONS

Nakajima et al (J. Electrochem. Soc., 129, 1982, pp. 141-143.*
Diefenderfer, Principles of Electronic Instrumentation, 2nd Edition, 1979, pp. 159, 226.*
Bettelheim, et al., "A New Polymer AglAgCl Reference Electrode for Electrochemistry with No Contacting Electrolyte Solution," Journal of the Electrochemical Society, 44, 1988, pp. 1041-1042.
Bin Yu et al, "Controllable Seolite Films on Electrodes—Comparing DC Voltage Electrophoretic Deposition and a Novel Pulsed Voltage Method," Electrochemistry Communications, vol. 4, No. 10, Oct. 2002, pp. 737-742.
Christiasen, "The Achilles' Heal of Potentiometric Measurements, the Liquid Junction Potential," IEEE Transactions of Biomedical Engineering, 33, 2, 1986, pp. 79-82.
Covington, A.K., et al., "Reference Electrodes and Liquid Juntion Effects in Ion-Selective Electrode Potentiometry," Ion Selective Review, 5, 1983, pp. 93-128.
Desmond, et al., "Evaluation of Miniaturized solid State Reference Electrode on A Silicon-Based Substrate," Sensor and Actuators B, 44, 1997, pp. 389-396.

(Continued)

Primary Examiner—Kaj K. Olsen
(74) Attorney, Agent, or Firm—Kris T. Fredrick (57) ABSTRACT

A reference electrode includes a conductive substrate having a first surface and an ionically insulating, hydrophobic layer adjacent to the first surface having a plurality of non-selective ion exchange sites.

25 Claims, 9 Drawing Sheets

OTHER PUBLICATIONS

Eine, et al., "Towards a Solid-State Reference Electrode," Sensors and Actuators B, 44, 1997, pp. 381-388.

Huang, et al., "A New Structured ISFET with Integrated Ti/Pd/Ag/AgCl Electrode and Micromachined Back-Side P+ Contacts," Journal of Chinese Institute of Engineers, 2002, 25(3), pp. 327-334.

Huang et al., "Fabrication and Characterization of a New Planar Solid-State Reference Electrode for ISFET Sensors," Thin Solid Films, 2002, 406(1-2), pp. 255-261.

Hyuk Jin Lee, et al., Solvent-Processible Polymer Membrane-Based Liquid Junction-Free Reference Electrode,: Anal. Chem., 70[16], pp. 3377-3383, Aug. 15, 1998.

Kwang-Seok, et al., "Analysis of Heavy-Metal Ions Using Mercury Microelectrodes and a Solid-State Reference Electrode on a Si Wafer," in Japan Soc. Appl. Phys. Japanese Journal of Applied Physics Part 1-Regular Papers Short Notes & Review Papers, vol. 39, No. 12B, Dec. 2000, pp. 7159-7163.

Levitchev, et al., "Photocurable Carbonate-Selective Membranes for chemical Sensors Containing Lipophilic Additives," Sensors and Actuators B.,44, 1997, pp. 397-401.

Margules, et al., "Functional Mechanisms of Polymer-Based in Vivo Reference electrodes," J. Biomed, Eng. 9, 1987, pp. 21-25.

Matysik et al., "A Disposable Electrode Based on Zeolite-Polymer Membranes for Potentiometric Titrations of Ionic Surfactants," Sensors and Actuators B-Chemical, vol. B85, No. 1-2, Jun. 20, 2002, pp. 104-108.

Matsuo, et al., "Characteristics of Reference Electrodes Using a Polymer Gate ISFET," Sensor and Actuators, 5, 1984, pp. 293-305.

Nagy, et al., "Promising New Solid-State Reference Electrode," Electrochemical Society Letters, 144, [1], 1977, L1-L2.

Sandifer, Theory of Interfacial Potential Differences: Effects of Adsorption onto Hydrated (Gel) and Nonhydrated Surfaces, Analytical Chemistry, 60, 1988, pp. 1553-1564.

Smith, R.L., et al, "An integrated Sensor for Electrochemical Measurements," IEEE Transactions on Biomedical Engineering, 33, 2, 1986, pp. 83-90.

Tahara, et al., "Electrochemical Reference Electrode for the Ion-Selective Field Effect Transistor," Chemistry Letters (The Chemical Society of Japan), 1982, pp. 307-310.

Yousefi, "Studies on Mixed Transition Metal Dichalcogenide-Electrolyte Interfaces," Crystal Research and Technology, 25, 6, 1990, pp. 125-129.

Yun, San Yong, et al., "Potentiometric Properties of Ion-Selective Electrode Membranes Based on Segmented Polyether Urethane Matrices," Journal of the American Chemical Society, 69, [5], 1977, pp. 868-873.

* cited by examiner

SOLID STATE REFERENCE ELECTRODE

FIELD OF THE INVENTION

The present invention generally relates to the field of solid state reference electrodes, and more particularly, to solid state electrochemical reference electrodes.

BACKGROUND OF THE INVENTION

In electrochemical measurements, a chemical "reference potential" is often used in conjunction with an electrochemical sensor such as, for example, a pH sensor. The reference potential is analogous to the ground potential in an electrical circuit. In most cases, the reference potential is derived from a reference electrode that is immersed in a separate reference cell, where the reference cell is in ionic communication with the test solution. Typically, the reference electrode develops a reference potential through insoluble silver or mercury salts that are in contact with their metals. In the reference cell, the salts are typically contained in a conducting, ionic solution that is in ionic contact with the test solution. The ionic contact between the ionic solution of the reference cell and the test solution is typically provided via a porous layer, which allows ions to flow from the reference cell to the test solution and vice versa. One problem with many of these systems is that if the ionic flow rate through the porous layer is too low, drift can be introduced into the measurement, and if the ionic flow rate is too high, the ionic solution can be a source of contamination to the test solution and visa versa.

SUMMARY OF THE INVENTION

The present invention generally relates to solid state electrochemical reference electrodes. Solid state electrochemical reference electrodes in accordance with the present invention may reduce measurement drift, as well contamination of the test solution. The solid state electrochemical reference electrodes of the present invention may also be fabricated in a more cost-effective and timely manner, and may be more reliable than many previous reference electrode configurations.

In one illustrative embodiment of the present invention, a reference electrode is provided that includes a conductive substrate that has a first surface and an ionically insulating, hydrophobic layer positioned adjacent to the first surface. The ionically insulating, hydrophobic layer has a plurality of non-selective ion exchange sites on its exposed surface. The ionically insulating, hydrophobic layer is exposed to the test solution, and because of the ion exchange sites, generates an ionic charge on the surface of the ionically insulating, hydrophobic layer. Because the ionically insulating hydrophobic layer is provided adjacent to the conductive substrate, a corresponding mirror charge is generated in the conductive substrate, which produces a corresponding reference potential in the conductive substrate. In some embodiments, a non-selective ion exchange layer is also provided on or in the ionically insulating hydrophobic layer to increase the number of exposed ion exchange sites, and thus the sensitivity of the reference electrode. In some embodiments, the non-selective ion exchange layer is a non-selective ion exchange zeolyte layer. However, it is recognized that any suitable non-selective ion exchange layer may be used, depending on the application.

In some embodiments, the reference potential generated on the conductive substrate is provided to a high impedance input of an electric circuit such as an amplifier or the like. For example, the reference potential may be provided to the gate of a Field Effect Transistor (FET), or any other suitable high impedance circuit. In other embodiments, the reference potential may be provided to the substrate of a FET. When so provided, the gate of the FET may be connected to the output of an electrochemical sensor within the test solution. The reference potential at the substrate may help offset or compensate the current supplied by the FET at a given gate voltage provided by the electrochemical sensor. Such a FET configuration may help provide a good chemical to electrical transducer.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular illustrative embodiments described. On the contrary, the intention is to cover all modifications, equivalents, and alternatives falling within the spirit and scope of the invention.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials may be illustrated for the various elements, those skilled in the art will recognize that many of the examples provided have suitable alternatives that may be utilized.

Generally, the present invention pertains to reference electrodes such as, for example, solid-state electrochemical reference electrodes. The present invention is applicable for use with all potentiometric, amperommetric, and voltammetric techniques, as desired. While the present invention is not so limited, an appreciation of various aspects of the invention will be gained through a discussion of the various illustrative embodiments and examples provided below.

Figure 1:
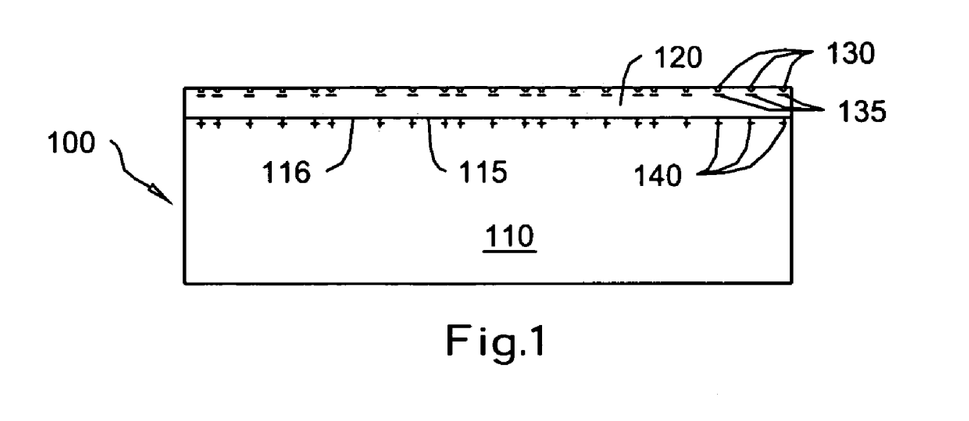
FIG. 1 is a cross-sectional view of a reference electrode according to an embodiment of the invention.

FIG. 1 is a cross-sectional view of a reference electrode 100 according to an illustrative embodiment of the invention. The reference electrode 100 includes a conducting substrate 110 having a first surface 115. An ionically insulating, hydrophobic layer 120 is provided adjacent to the conducting substrate 110 first surface 115. The ionically insulating, hydrophobic layer 120 has a plurality of non-selective ion exchange sites 130 that may be on or near an outer surface of the ionically insulating, hydrophobic layer 120.

The conducting substrate 110 can be any electrically conductive material capable of forming an image charge 140. In some embodiments, the conducting substrate 110 can be, for example, any metal or semiconductor material, as desired, and can be any suitable size. Alternatively, or in addition, the conducting substrate 110 can include a non-conducting substrate with a conducting layer provided thereon.

The ionically insulating, hydrophobic layer 120 can be any ionically insulating, hydrophobic material. In one illustrative embodiment, the ionically insulating, hydrophobic layer 120 is non-porous, non-reactive and non-hydrating. The ionically insulating, hydrophobic layer 120 of the illustrative embodiment can also be chemically inert, thermally stable, mechanically stable, readily processable using standard IC processing techniques (spin coating, ion milling, etc.) provide a stable reference potential over a pH range of 1-14, provide low interference background ionic strength, and/or demonstrate low potential drift over time.

In some embodiments, the ionically insulating, hydrophobic layer 120 may be a polymer or an amorphous polymer. For example, the ionically insulating, hydrophobic layer 120 can be polytetrafluoroethylene, amorphous polytetrafluoroethylene, polystyrene, polyethylene, polypropylene, polycarbonate, polymethyl methacrylate, parylene, or mixtures thereof. Illustrative examples of useful ionically insulating, hydrophobic layer 120 material includes Teflon AF™ from DuPont, FluoroPel™ from Cytronics, or any other suitable ionically insulating hydrophobic layer material or material composition.

The ionically insulating, hydrophobic layer 120 can have any thickness, however, it is preferable that the ionically insulating, hydrophobic layer 120 be as thin as possible, preferably less than or equal to 1 micron, but this is not required in all embodiments. In some embodiments, the ionically insulating, hydrophobic layer 120 has a thickness of 0.1 micron to 10 micron, 0.1 micron to 5 micron, or 0.5 micron to 1 micron.

The plurality of non-selective ion exchange sites 130 can be formed from simple impurities on the ionically insulating, hydrophobic layer 120 surface. Alternatively, or in addition, the plurality of non-selective ion exchange sites 130 may include zeolyte particles. The non-selective ion exchange sites 130 allow the intercalation of background ions (cations or anions) from a sample fluid. The non-selective ion exchange sites 130 strips the ions (such as cations) from their hydrated surroundings and establishes a surface charge 135, and thus an accompanying image charge 140 on the underlying conductive substrate 110. The image charge represents the reference potential on the conductive substrate 210.

In electrochemical measurements, background ion concentrations can be many orders of magnitude greater than analyte concentrations. In many cases, a usable reference potential results when a non-selective ion exchange site 130 is used on the hydrophobic layer 120. A useful non-selective ion exchange site 130 particle is a zeolyte. Zeolyte particles can be disposed on the hydrophobic layer 120 in any useful amount to create a desired ion exchange site density. Useful zeolyte particles have a pore size that is greater than or equal to the size of an ammonium ion. Examples of commercial zeolytes from Zeolyte, International (Valley Forge, Pa.) are available under the tradenames; CBV5524, CP814E, CP814N and simple alumina ($Al_2Si_2O_7$).

An adhesion promoter 116 can be disposed between the conductive substrate 110 and the ionically insulating, hydrophobic layer 120, but this is not required in all embodiments. The adhesion promoter 116 can be any material that helps join the ionically insulating, hydrophobic layer 120 to the remaining reference electrode 100. In some embodiments, the adhesion promoter 116 can be a siloxane such as, for example, hexamethyl disiloxane, and the like.

Figure 2:
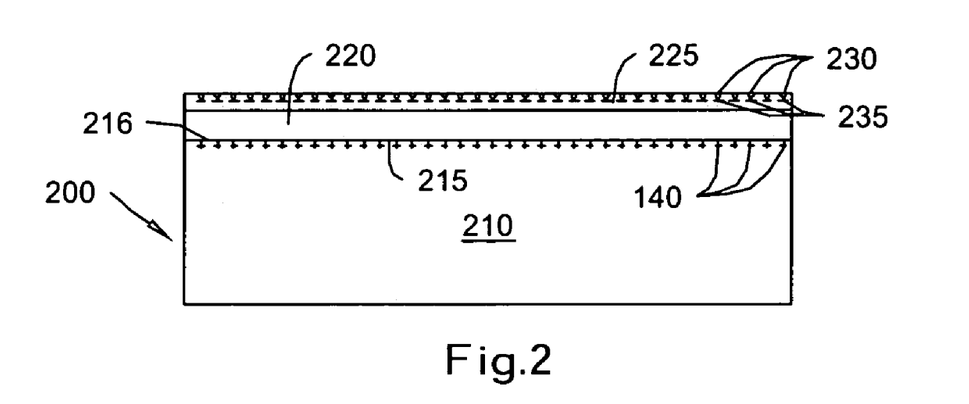
FIG. 2 is a cross-sectional view of a reference electrode according to an embodiment of the invention.

FIG. 2 is a cross-sectional view of a reference electrode 200 according to another illustrative embodiment of the present invention. The reference electrode 200 includes a conducting substrate 210 having a first surface 215. An ionically insulating, hydrophobic layer 220 is provided adjacent to the conducting substrate 210 first surface 215. A non-selective ion exchange layer 225 is disposed on the ionically insulating, hydrophobic layer 220.

The conducting substrate 210 and the hydrophobic layer 220 can be similar to that described above. In the illustrative embodiment, the non-selective ion exchange layer 225 includes non-selective ion exchange sites sufficient in quantity to achieve a desired ion exchange site density. In some embodiments, the non-selective ion exchange sites, shown at 230, are provided by non-selective ion exchange particles that are provided in sufficient density to constitute a layer 225, and may be formed with zeolyte particles. Like above, and in some embodiments, an adhesion promoter 216 can be disposed between the conductive substrate 210 and the ionically insulating, hydrophobic layer 220 as described above.

The non-selective ion exchange sites 330 allow the intercalation of background ions (cations or anions) from the sample fluid. The non-selective ion exchange sites 230 strip the ions (such as cations) from their hydrated surroundings and establishes a surface charge 235 on the non-selective ion exchange layer 225, when then produces an accompanying image charge 240 on or in the underlying conductive substrate 210. The image charge produces the reference potential on or in the conductive substrate 210.

Figure 3:
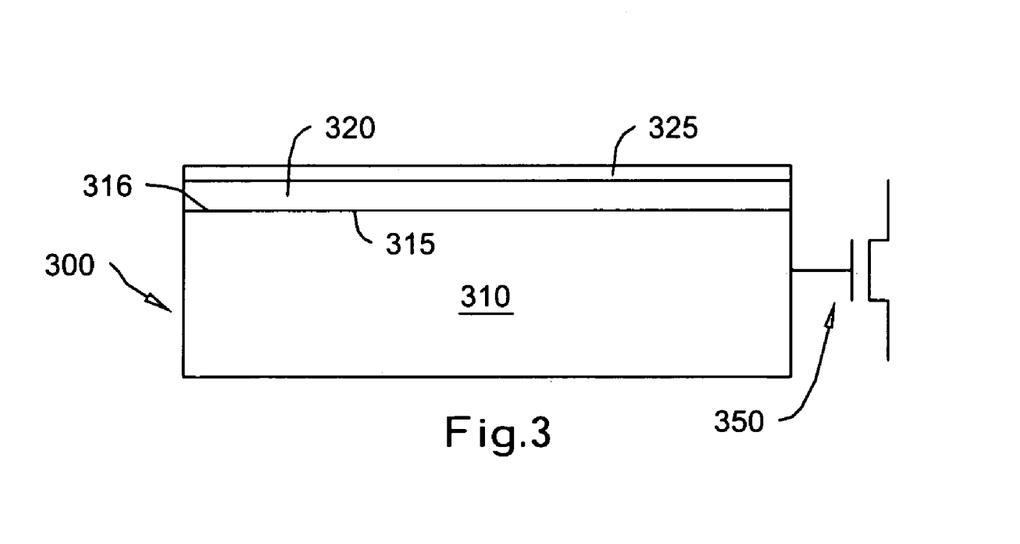
FIG. 3 is a cross-sectional view of a reference electrode electrically coupled to a field effect transistor.

FIG. 3 is a cross-sectional view of a reference electrode 300 that is coupled to the gate of a Field Effect Transistor (FET). The reference electrode 300 of FIG. 3 may be similar to the reference electrode 200 of FIG. 2. However, in the illustrative embodiment of FIG. 3, the conductive substrate 310 of the reference electrode 300 is electrically coupled to the gate of a FET device 350, as shown. While a FET device 350 is shown, it is contemplated that the conductive substrate 310 may be electrically coupled to any suitable electrical device or circuit, as desired. The conductive substrate 310 is preferably electrically coupled to a relatively high impendence input of an electrical device or circuit.

Figure 4:
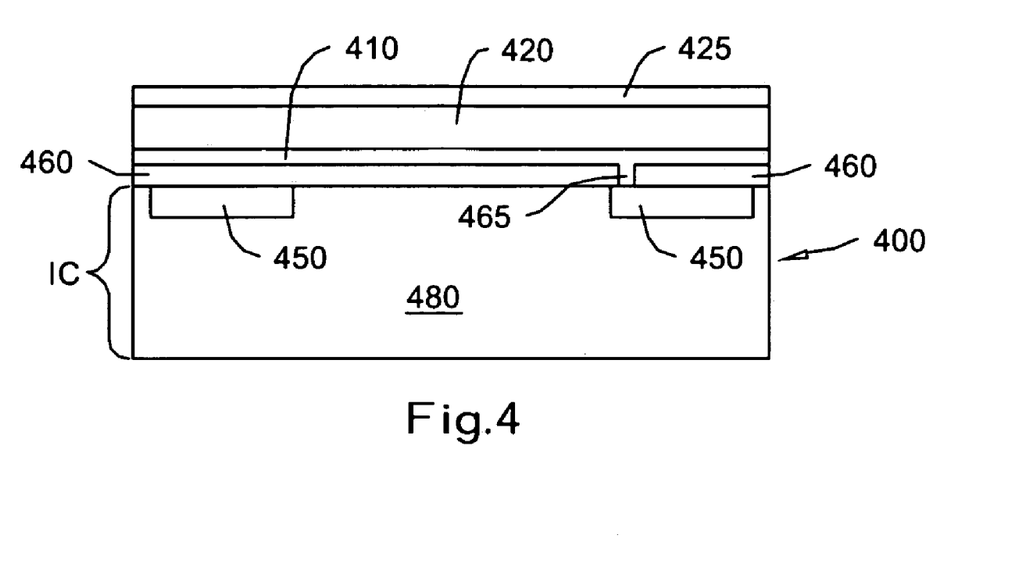
FIG. 4 is a cross-sectional view of a reference electrode according to an embodiment of the invention.

FIG. 4 is a cross-sectional view of a reference electrode 400 according to yet another illustrative embodiment of the present invention. The reference electrode 400 includes a conducting substrate 410, with an ionically insulating, hydrophobic layer 420 positioned adjacent to the conducting substrate 410. A non-selective ion exchange layer 425 is shown disposed on or adjacent to the ionically insulating, hydrophobic layer 420.

In the illustrative embodiment, the conducting substrate 410 is disposed on a dielectric layer 460. The dielectric layer 460 is shown disposed on an integrated circuit substrate 480 that includes electronics 450 previously formed therein. The electronics 450 may include one or more conductive interconnect pads that are adapted to electrically interconnect to the conducting substrate 410 of the reference electrode 400. In the illustrative embodiment shown, a VIA 470 is formed through the dielectric layer 460 to electrically connect the conductive substrate 410 and the one or more conductive interconnect pads of electronics 450. The electronics may be used to process the reference potential provided by the conducting substrate 410, preferably in conjunction with one or more electrical signals provided by one or more electrochemical sensors disposed in the test solution.

Figure 5:
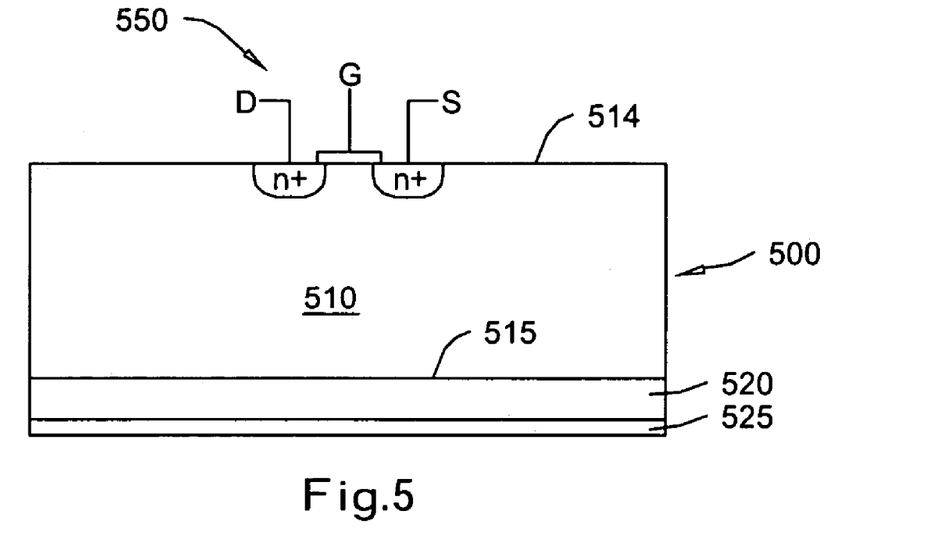
FIG. 5 is a cross-sectional view of a reference electrode according to an embodiment of the invention.

FIG. 5 is a cross-sectional view of a reference electrode 500 according to yet another illustrative embodiment of the present invention. The reference electrode 500 includes a conducting substrate 510. In this case, the conducting substrate 510 is a semiconductor wafer. An ionically insulating, hydrophobic layer 520 is added adjacent to the conducting substrate 510 first surface 515. A non-selective ion exchange layer 525 may be disposed on the ionically insulating, hydrophobic layer 520, as described above. In this embodiment, the ionically insulating, hydrophobic layer 520 and the non-selective ion exchange layer 525 are provided on the back side of the semiconductor wafer.

Electronics 550 may be fabricated into the front side of the semiconductor wafer, as shown. In the illustrative embodiment, electronics 550 include a FET device. As can be seen, the substrate of the FET device 550 corresponds to the conducting substrate 510 of the reference electrode 500. Thus, the reference potential on the conducting substrate 510 is provided to the substrate of the FET device 550. When so provided, the gate of the FET device 550 may be connected to the output of an electrochemical sensor that is in the test solution. The reference potential then may help offset or regulate the current supplied by the FET device 550 for a given gate voltage provided by the electrochemical sensor. Such a configuration may help provide a good chemical to electrical transducer.

EXAMPLES

Experimental Arrangement

The following examples were tested using a test fixture. This test fixture was a pH sensor and was designed and fabricated as described below.

In this test fixture, a polycarbonate tube fitted with an O-ring seal on the bottom was clamped against a standard 3" silicon wafer forming a liquid-tight reservoir. Three-inch silicon wafers were chosen as the substrate because they are inexpensive, readily available, easily processed using available equipment and have well-controlled electrical and surface characteristics. The wafer was supposed against an aluminum base, which also provided a convenient means for making electrical contact to it. The hydrophobic, ionically insulating material under investigation was coated onto the top surface of the wafer and the potential of the coated surface was monitored against a standard pH probe and double junction Ag/AgCl reference probe through an Orion pH meter. The output was also recorded on a strip chart recorder to monitor stability and drift using buffers of pH 4, 6, 8 and 10.

Material Evaluations

To help evaluate the inventive approach, several sample materials were acquired including Parylene (poly-p-xylene). Parylene samples ("C" and "H") were obtained from Specialty Coating Systems, Inc., (Clear Lake, Wis.), who specialize in vacuum deposition of parylene and other conformal coatings. Samples of Parylene "C", a standard commercial grade material and Parylene "H", a higher density material with lower water absorption were obtained as 0.5 μm pinhole free films on 3" silicone wafers (HTC supplied wafers). The films were tested in the test apparatus described in Part I, and the results are seen in FIG. 6.

Figure 6:
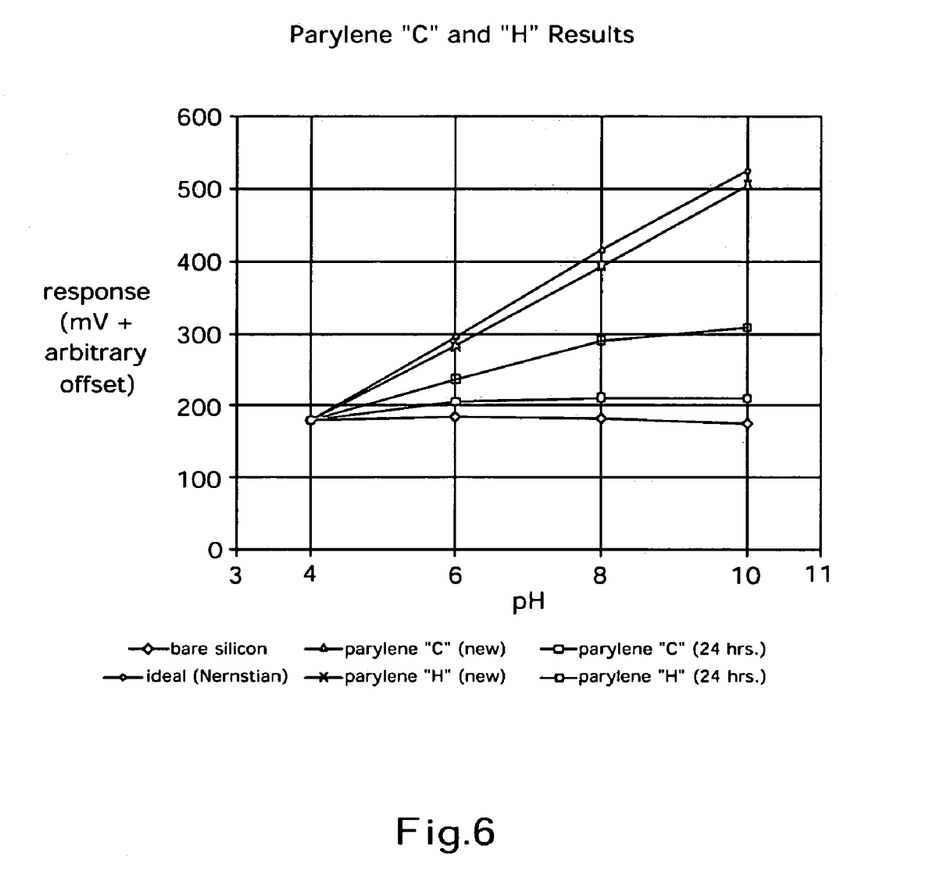
FIG. 6 is a graph of pH meter response (mV) using the inventive reference electrode over a pH range of 4 to 10 with Parylene "C" and Parylene "H" as an ionically insulating, hydrophobic layer.

One can see that although the initial results in FIG. 6 look very good, with almost Nemstrian response, the film quickly beings to degrade and then approaches the response of bare silicon. Since the material is vacuum deposited from an extremely pure state, pin holes and entrained impurities are an unlikely cause of this failure. More likely, this is a result of water absorption and ionic conduction through the film. Parylene is intended to be used as a thick film environmental coating with low (total) water absorption. In this application, water penetration in the first few microns of the material is inconsequential. In our case, however, the total film thickness is <1 μm and even minor water absorption into the film has an effect over time. From the graph, we can also see that the effect is cumulative implying a gradual increase in ion conductivity rather than a sudden failure such as a loss of adhesion and lift off of the surface.

Teflon AF

A second material evaluated was Teflon AF (poly-tetrafluroethylene). Samples of Teflon AF (1601S) were obtained from: DuPont Fluoproducts (Wilmington, Del.). The material was received as a 6% w/w solution in FC-75 (a perfluronated hydrocarbon solvent from 3M). Wafers with native oxide were then spin-coated at 3000 RPMs for 30-40 seconds to get a 0.5 to 1 micron coating. After coating, the wafers were baked at 160° C. for at least 10 minutes to boil off excess solvent and cure the polymer film. Elipsometry of the films indicated an average thickness of approximately 0.6 μm with an index of refraction of 12.3, which is consistent with the manufacturer's specifications.

These films could be peeled from the substrate by rubbing a finger across them, and completely lifted off immediately on contact with our test buffers. Therefore, several methods of surface preparation were tried.

First, polished wafers were prebaked at 160° C. for 1 hour and then wetted with FC75 to remove surface contamination and adsorbed water. This resulted in films that were mechanically stable to abrasion with a finger, but still lifted off over the course of 24-48 hours when in contact with water. We modified the procedure to mechanically roughen the surface by bead blasting and followed by baking and wetting. Bead blasted wafers were significantly more mechanically stable and allowed us to take measurements over several days before failing by lift off.

In addition, we used a siloxane, hexamehtyl disiloxane (HMDS), as a surface pretreatment. Here the bead blasted (or polished) wafers were exposed to HMDS vapor for 5 minutes followed immediately by wetting with FC-75 and spin coating as described above. These films, on both bead blasted and polished wafers, were well adhering and stable in contact With water.

Figure 7:
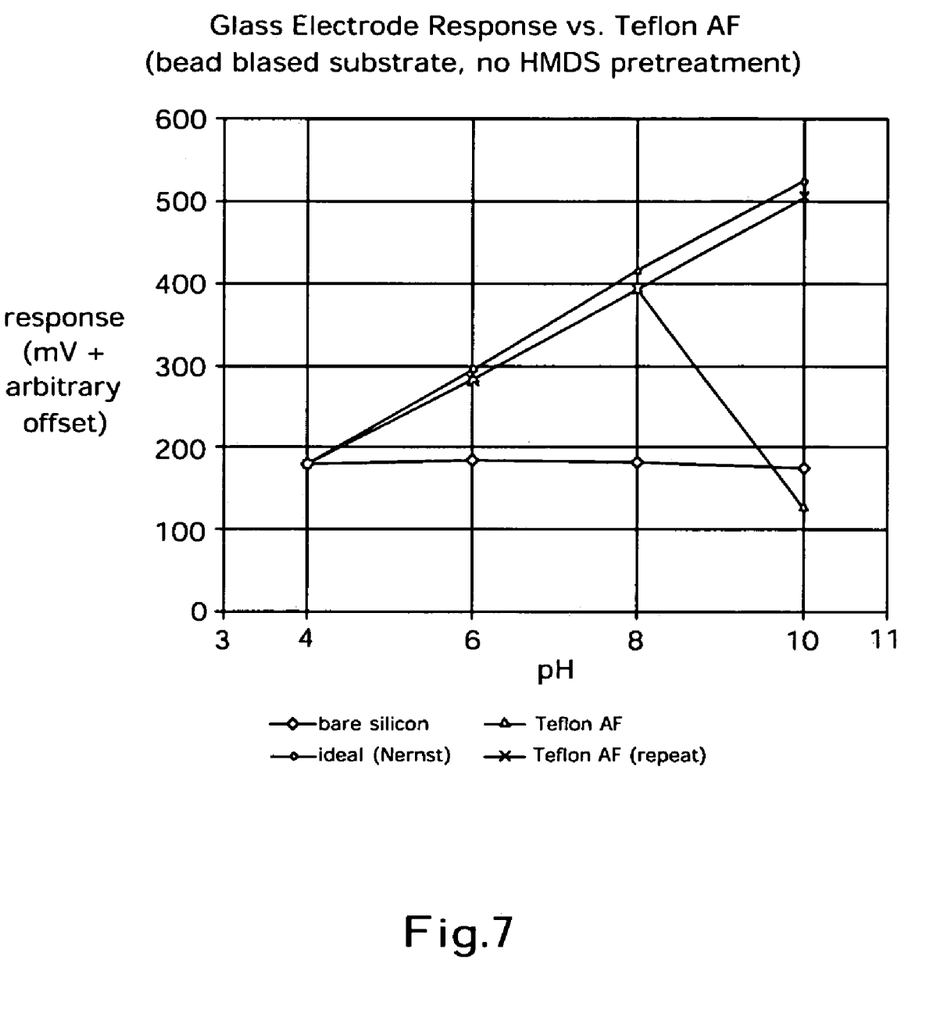
FIG. 7 is a graph of pH meter response (mV) using the inventive reference electrode over a pH range of 4 to 10 with Teflon AF as an ionically insulating, hydrophobic layer.

The Telfon AF material shows a very good reference response. Typical results for Teflon AF with only bead blasting as a surface pretreatment is seen in FIG. 7. One can see that the initial response of the material is very good, being very linear and almost Nemstian. Our glass electrode was measured to be Nemstian versus a standard Ag/AgCI double junction reference. By contrast, silicon alone shows an almost flat response, indicative of the fact that it is responding to pH in the same manner that the glass electrode did.

Figure 8:
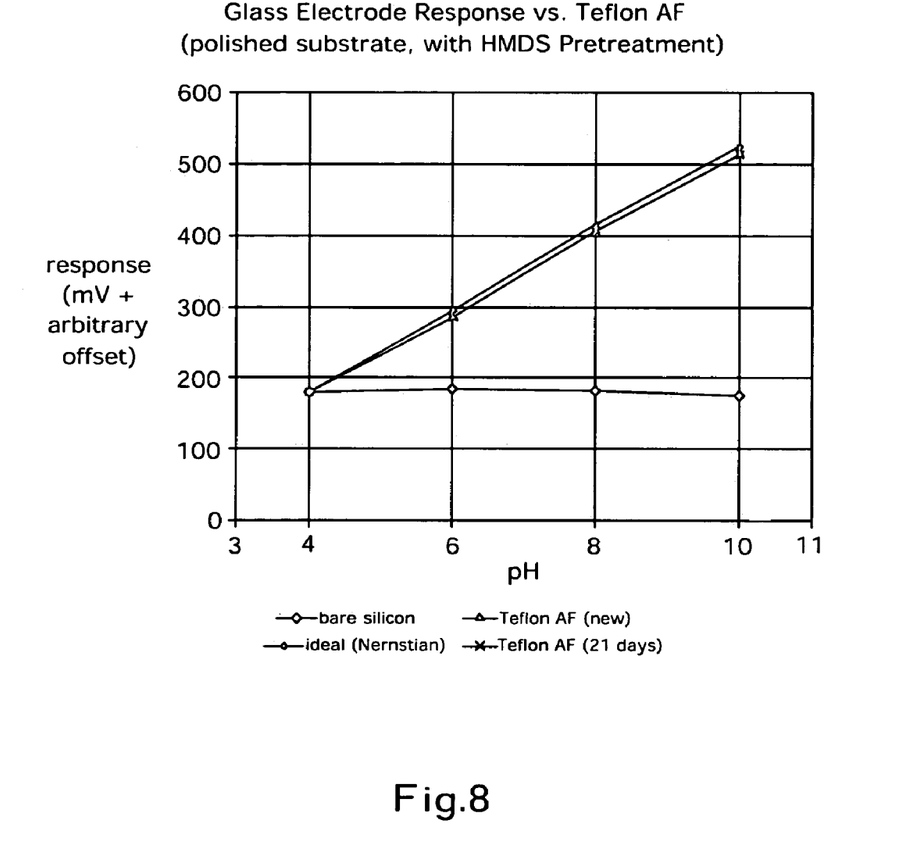
FIG. 8 is a graph of pH meter response (mV) using the inventive reference electrode over a pH range of 4 to 10 with Teflon AF as an ionically insulating, hydrophobic layer and HMDS pretreatment.

The same material using an HMDS pretreatment to promote adhesion is seen in FIG. 8. One can see that the material exhibits a nearly Nernstian response with no sign of failure after 21 days of exposure.

Zeolyte Modifications

Figure 9:
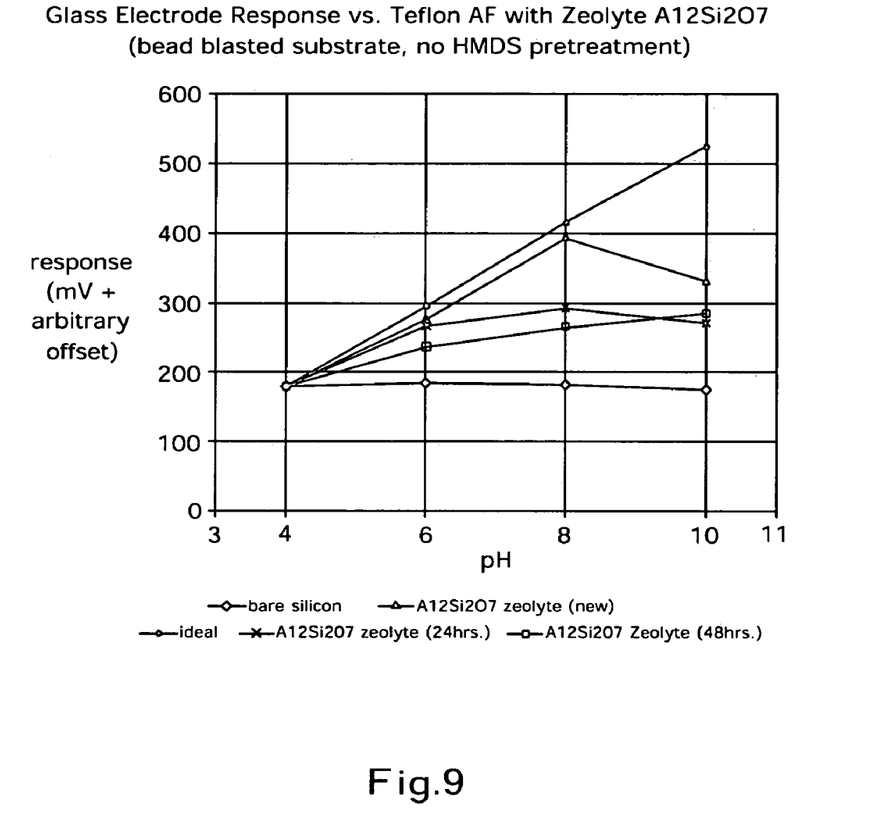
FIG. 9 is a graph of pH meter response (mV) using the inventive reference electrode over a pH range of 4 to 10 with Teflon AF as an ionically insulating, hydrophobic layer and $Al_2Si_2O_7$ zeolyte.

In order to modify the surface ion-exchange site density of the Teflon AF material, samples of various zeolytes were obtained from Zeolyst, International (Valley Forge, Pa.). These included their designations: CBV5524G (lot number 1822-18), CP814E (lot number 1822-35), CP814N, and a simple alumina which we designate $Al_2Si_2O_7$. These materials were applied to the Teflon surface by sprinkling it over the still tacky Teflon before baking, thereby mechanically embedding it in the surface. After baking, the excess zeolyte is removed with a light stream of distilled water. Films with zeolyte on the surface do show significantly modified behavior over native Teflon AF. CBV and alumina grades showed almost identical behavior as seen in FIG. 9.

Unlike the native Teflon described above, these films show distinctly sub-Nernstian and non-linear behavior even when freshly made. After a few hours, the response slowly degrades towards a "silicon-like" behavior. This behavior is consistent with the nature of alumina and silicates that freely exchange protons. The embedded material does strongly affect the behavior of the film. This implies that zeolyte selection can tailor film characteristics.

Figure 10:
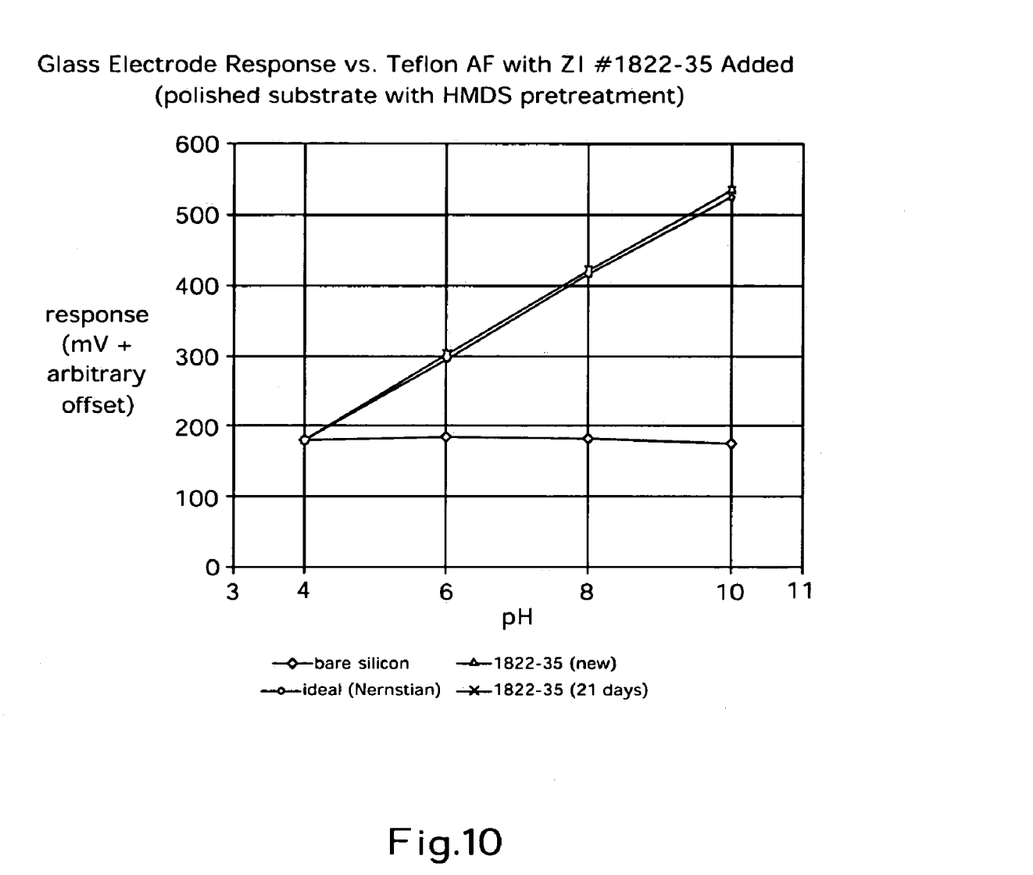
FIG. 10 is a graph of pH meter response (mV) using the inventive reference electrode over a pH range of 4 to 10 with Teflon AF as an ionically insulating, hydrophobic layer and CP814E (lot number 1822-35) zeolyte.

The lot number 1822 grade materials show better reference characteristics than alumina. CBV5524G (lot number 1822-18) and CP814E (lot number 1822-35) are size exclusion zeolytes with an internal cavity to accommodate large ammonium ions. Smaller ions all freely exchange with the cavity with no preference toward chemical nature. This is almost the ideal case for a reference electrode where "ion non-specificity" may be important. FIG. 10 shows the typical result for CP814E (lot number 1822-35). Again, like with Teflon AF alone, the response is very linear, although slightly super-Nernstian.

Figure 11:
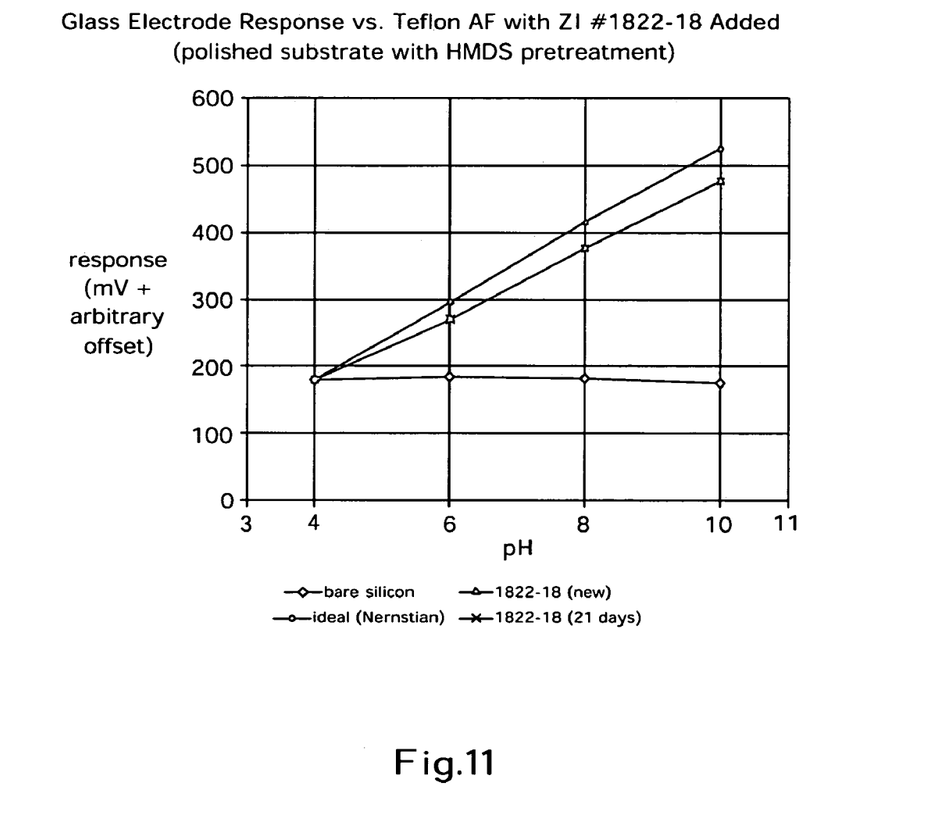
FIG. 11 is a graph of pH meter response (mV) using the inventive reference electrode over a pH range of 4 to 10 with Teflon AF as an ionically insulating, hydrophobic layer and CBV5524G (lot number 1822-18) zeolyte.

Zeolyte CBV5524G (lot number 1822-18) has somewhat smaller pore size than CP814E (lot number 1822-35). As a result, as seen in FIG. 11, its response is more understandably sub-Nernstian, having some small ion- and proton-exchange favoritism owing to its smaller pore size. Both materials are very stable over time (21 days) so long as material adhesion is maintained. Both materials significantly may enhance the speed of response of the film over native Teflon and permit smaller feature sizes as a result of a greatly increased ion-exchange site density.

Total Ionic Strength

Experiments were performed to check the response of the film to total ionic strength of the test solution. If the film is generating a "reference potential" based on simple space charging of the surface rather than as a result of nonspecific ion exchange with the test solution, the zero point will change with total ionic strength of the test solution. In some cases, this would be an unacceptable behavior as the ionic strength of the field environment is uncontrolled.

Figure 12:
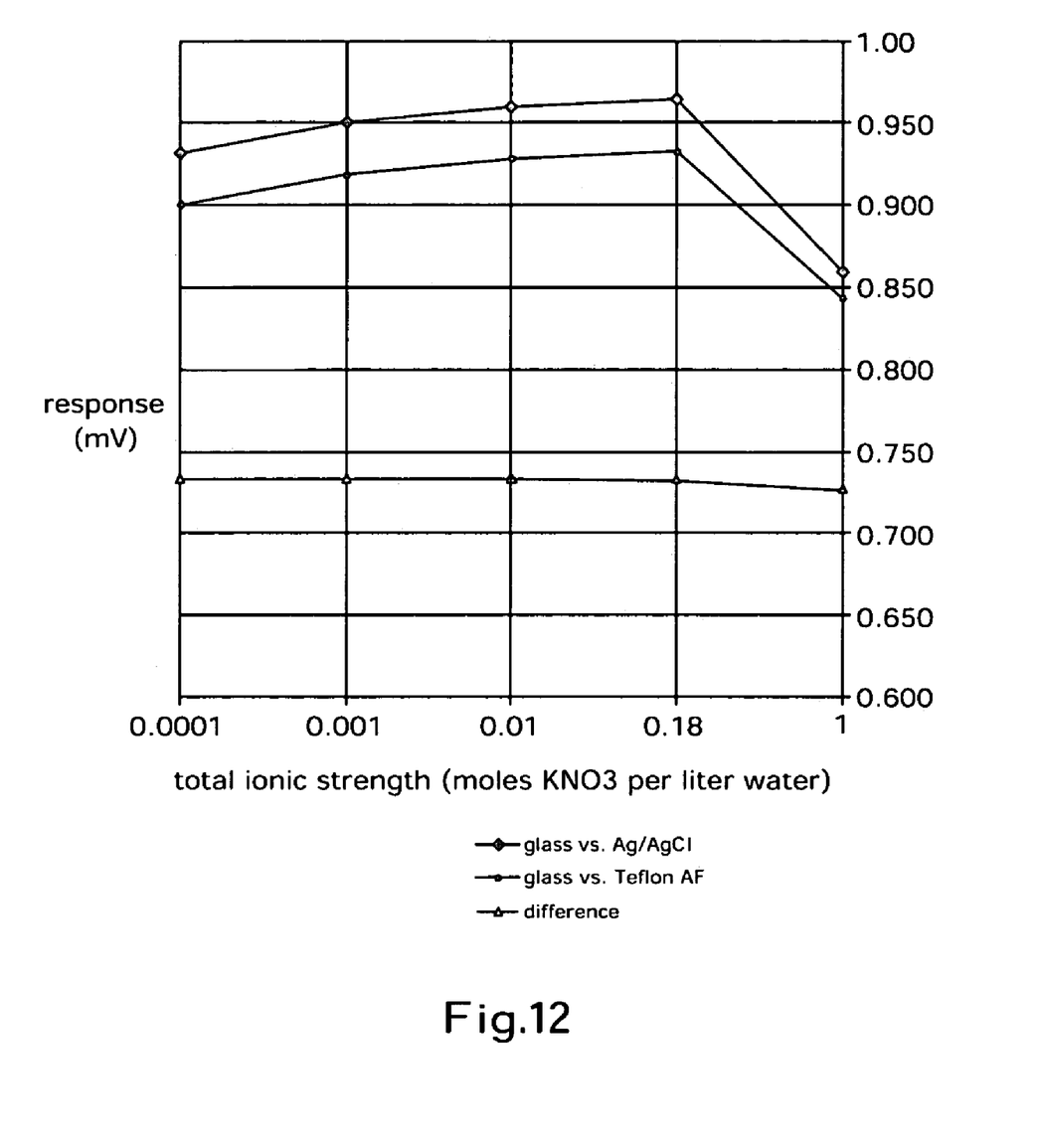
FIG. 12 is a graph of glass electrode response (mV) versus Ag/AgCl and Teflon AF film as a function of total ionic strength.

To examine this behavior, we tested solutions varying in total ionic strength from $1\times10^{-4}$M to 1.0M. The test solutions were unbuffered $KNO_3$ in deionizer water and the tests were run at room temperature. The response of a glass electrode versus a standard Ag/AgCI reference and our test film are seen in FIG. 12.

Because the solutions were unbuffered, the pH of the test solution varies with impurities in our $KNO_3$ salt, dissolved $CO_2$ and the like. We assume that at a maximum of 1M concentration, ion pairing and similar phenomenon are as yet insignificant. As a result the absolute value of the response of the glass electrode changes from solution to solution in response to pH. The result, however, is that the difference between the two responses is constant and varies by no more than 5 mV (at 1M concentration) over 4 decades of ionic strength. Because of this behavior, the mechanism of the response of the film is unlikely to be surface space charging based on ionic strength and we are indeed seeing true ion exchange with some moiety on the surface.

The present invention should not be considered limited to the particular examples described above, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

What is claimed is:

1. An electrochemical reference electrode comprising:
   a conductive substrate having a first surface; and
   an ionically insulating, hydrophobic layer comprising polytetrafluoroethylene adjacent to the first surface having a plurality of non-selective ion exchange sites comprising zeolite, the hydrophobic layer adapted to be exposed to a test solution.

2. The electrochemical reference electrode according to claim 1, wherein the conductive substrate is silicon.

3. The electrochemical reference electrode according to claim 1, wherein the conductive substrate includes a metal.

4. The electrochemical reference electrode according to claim 1, wherein the conductive substrate includes a non-conductive substrate with a conductive layer provided thereon.

5. The electrochemical reference electrode according to claim 1, wherein the ionically insulating, hydrophobic layer has a thickness of less than 1 micron.

6. The electrochemical reference electrode according to claim 1, further comprising an adhesion promoter disposed between the conductive substrate and the ionically insulating, hydrophobic layer.

7. The electrochemical reference electrode according to claim 6, wherein the adhesion promoter comprises a siloxane.

8. The electrochemical reference electrode according to claim 1, wherein the conductive substrate is electrically coupled to an amplifier.

9. The electrochemical reference electrode according to claim 1, wherein the conductive substrate is electrically coupled to a field effect transistor.

10. An electrochemical reference electrode comprising:
   a conductive substrate having a first surface; and
   an ionically insulating, hydrophobic layer comprising polytetrafluoroethylene adjacent to the first surface; and
   a non-selective ion exchange layer disposed on or in the ionically insulating, hydrophobic layer comprising zeolite.

11. The electrochemical reference electrode according to claim 10, wherein the conductive substrate is silicon.

12. The electrochemical reference electrode according to claim 10, wherein the conductive substrate includes a metal.

13. The electrochemical reference electrode according to claim 10, wherein the conductive substrate includes a non-conductive substrate with a conductive layer provided thereon.

14. The electrochemical reference electrode according to claim 10, wherein the ionically insulating, hydrophobic layer has a thickness of less than 1 micron.

15. The electrochemical reference electrode according to claim 10, further comprising an adhesion promoter disposed between the conductive substrate and the ionically insulating, hydrophobic layer.

16. The electrochemical reference electrode according to claim 15, wherein the adhesion promoter comprises a siloxane.

17. The electrochemical reference electrode according to claim 10, wherein the conductive substrate is electrically coupled to an amplifier.

18. The electrochemical reference electrode according to claim 10, wherein the conductive substrate is electrically coupled to a field effect transistor.

19. A solid state electrochemical reference electrode comprising:
   a conductive substrate having a first surface;
   an ionically insulating, hydrophobic layer comprising polytetrafluoroethylene adjacent to the first surface having a plurality of non-selective ion exchange sites comprising zeolite; and
   a field effect transistor having a gate, source, drain and substrate, wherein the conductive substrate is electrically connected to the substrate.

20. The solid state electrochemical reference electrode according to claim 19, wherein the conductive substrate is silicon.

21. The solid state electrochemical reference electrode according to claim 19, wherein the conductive substrate includes a metal.

22. The solid state electrochemical reference electrode according to claim 19, wherein the conductive substrate includes a non-conductive substrate with a conductive layer provided thereon.

23. The solid state electrochemical reference electrode according to claim 19, wherein the ionically insulating, hydrophobic layer has a thickness of less than 1 micron.

24. The solid state electrochemical reference electrode according to claim 19, further comprising an adhesion promoter disposed between the conductive substrate and the ionically insulating, hydrophobic layer.

25. The solid state electrochemical reference electrode according to claim 24, wherein the adhesion promoter comprises a siloxane.

* * * * *